(12) United States Patent
Jung (10) Patent No.: US 10,438,589 B2
(45) Date of Patent: *Oct. 8, 2019

(54) ROBOT APPARATUS AND METHOD FOR REGISTERING SHORTCUT COMMAND THEREOF BASED ON A PREDETERMINED TIME INTERVAL

(71) Applicant: Samsung Electronics Co., Ltd., Suwon-si, Gyeonggi-do (KR)

(72) Inventor: Hyun-ryong Jung, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/958,349

(22) Filed: Apr. 20, 2018

(65) Prior Publication Data

US 2018/0240461 A1    Aug. 23, 2018

Related U.S. Application Data

(63) Continuation of application No. 12/318,053, filed on Dec. 19, 2008, now Pat. No. 9,953,642.

(30) Foreign Application Priority Data

Jun. 3, 2008   (KR) ......................... 10-2008-0052151

(51) Int. Cl.
*G10L 15/22* (2006.01)
*G06F 19/00* (2018.01)
(Continued)

(52) U.S. Cl.
CPC ............ *G10L 15/22* (2013.01); *G10L 15/265* (2013.01); *G06F 19/3462* (2013.01); *G16H 20/13* (2018.01); *G16H 40/63* (2018.01)

(58) Field of Classification Search
CPC ........ G10L 15/22; G10L 15/265; B25J 13/00; G06F 19/3462
(Continued)

(56) References Cited

U.S. PATENT DOCUMENTS 5,774,841 A * 6/1998 Salazar ................... G10L 15/22
704/225
6,735,632 B1   5/2004 Kiraly et al.
(Continued)

FOREIGN PATENT DOCUMENTS

| JP | 2000-112493 | 4/2000 |
|---|---|---|
| KR | 10-2002-0088880 | 11/2002 |
| KR | 10-0810500 | 3/2008 |

OTHER PUBLICATIONS

Korean Office Action dated Sep. 30, 2014 in Korean Patent Application No. 10-2008-0052151.
(Continued)

*Primary Examiner* — Farzad Kazeminezhad
(74) *Attorney, Agent, or Firm* — Staas & Halsey LLP (57) ABSTRACT

A robot apparatus including an input unit to receive a voice command from a user, a determination unit to determine whether a voice command is repeated a predetermined number of times, and a control unit to register a shortcut command to shorten a voice command if it is determined a voice command is repeated a predetermined number of times. A shortcut command to shorten a voice command of a user is generated, and thus user convenience is enhanced.

14 Claims, 8 Drawing Sheets

(51) Int. Cl.
*G10L 21/00* (2013.01)
*G10L 15/26* (2006.01)
*G16H 20/13* (2018.01)
*G16H 40/63* (2018.01)

(58) Field of Classification Search
USPC .................................. 704/275, 225; 700/245
See application file for complete search history.

(56) References Cited

U.S. PATENT DOCUMENTS

| | | | | |
|---|---|---|---|---|
| 9,953,642 | B2* | 4/2018 | Jung | ................ G10L 15/22 |
| 2001/0021909 | A1* | 9/2001 | Shimomura | ............ G10L 15/22 |
| | | | | 704/275 |
| 2003/0023348 | A1* | 1/2003 | Inoue | ....................... B25J 13/00 |
| | | | | 700/245 |
| 2005/0102066 | A1 | 5/2005 | Watanabe et al. | |

OTHER PUBLICATIONS

U.S. Notice of Allowance dated Dec. 15, 2017 in U.S. Appl. No. 12/318,053.
U.S. Office Action dated May 19, 2017 in U.S. Appl. No. 12/318,053.
U.S. Office Action dated Sep. 13, 2013 in U.S. Appl. No. 12/318,053.
U.S. Office Action dated Mar. 26, 2013 in U.S. Appl. No. 12/318,053.
U.S. Office Action dated Sep. 18, 2013 in U.S. Appl. No. 12/318,053.
U.S. Office Action dated Mar. 21, 2012 in U.S. Appl. No. 12/318,053.
U.S. Decision on Appeal dated Jan. 3, 2017 in U.S. Appl. No. 12/318,053.
U.S. Examiner's Answer to Appeal Brief dated Jul. 16, 2014 in U.S. Appl. No. 12/318,053.
Notice of Panel Decision from Pre-Appeal Brief Review dated Mar. 5, 2014 in U.S. Appl. No. 12/318,053.
U.S. Appl. No. 12/318,053, filed Dec. 19, 2008, Hyun-ryong Jung, Samsung Electronics Co., Ltd.

* cited by examiner

| 310 | 320 | 330 | 340 | 350 |
|---|---|---|---|---|
| "get me the TV remote" | Action | Object Context | Condition Context | Count |

| 310 | 320 | 330 | 340 | 350 |
|---|---|---|---|---|
| "turn off the living room light" | Action | Object Context | Condition Context | Count |

| 310 | 320 | 330 | 340 | 350 |
|---|---|---|---|---|
| "get me the TV remote" | register a shortcut command | Object Context | Condition Context | Count |

ROBOT APPARATUS AND METHOD FOR REGISTERING SHORTCUT COMMAND THEREOF BASED ON A PREDETERMINED TIME INTERVAL

CROSS-REFERENCE TO RELATED APPLICATIONS

This application is a continuation of U.S. patent application Ser. No. 12/318,053 filed Dec. 19, 2008, which claims the benefit of Korean Patent Application No. 10-2008-0052151, filed in the Korean Intellectual Property Office on Jun. 3, 2008, the disclosures of which are incorporated herein by reference.

BACKGROUND

1. Field

Aspects of embodiments of the present invention relate to a robot apparatus and a method for registering a shortcut command thereof, and more particularly, to a robot apparatus to generate a shortcut command so as to shorten a voice command, and a method for registering a shortcut command thereof.

2. Description of the Related Art

With advances in mechanical and electronic fields, robot technology has become widely developed. Recently, humanoid robots which operate according to a human voice command have become widespread.

Robot apparatuses require complex command systems, unlike appliances and communication apparatuses. Therefore, it may be inconvenient for a user to manipulate a robot, and a robot may conduct an operation different from that commanded by the user since the robot misunderstands the user command.

If a robot receives a voice command from a user, the robot requires a process of converting the voice into a language recognized by the robot. For example, if a user tells a robot "I'm going to bed, so turn off the TV, check the gas valve, and check that the front door is locked." However, the robot may misunderstand the commands or perform them incorrectly since the commands are so long.

If the command issued to the robot is long, repeating the command may cause inconvenience for a user.

SUMMARY

Aspects of embodiments of the present invention relate to a robot apparatus to generate a shortcut command to shorten a voice command of a user, and a method for generating a shortcut command.

Additional aspects and/or advantages will be set forth in part in the description which follows and, in part, will be apparent from the description, or may be learned by practice of the invention.

To achieve the above and/or other aspects and advantages, embodiments of the present invention include a robot apparatus including an input unit to receive a voice command from a user, a determination unit to determine whether the voice command is repeated a predetermined number of times, and a control unit to register a shortcut command to shorten the voice command if it is determined that the voice command is repeated the predetermined number of times.

The robot apparatus may further include a driving unit to operate according to the voice command, wherein if the registered shortcut command is input through the input unit, the control unit controls the driving unit to operate according to the voice command corresponding to the shortcut command which is received.

If it is determined that the voice command is repeated the predetermined number of times, the control unit may inquire as to whether to register the shortcut command to shorten the voice command of the user.

The control unit may receive the shortcut command to be registered in response to the inquiry.

The robot apparatus may further include a storage unit to store a plurality of scripts including a command, an operation performed according to the command, a subject of the operation, a condition for performing the operation, and a number of times the command is input, wherein if the shortcut command is input, the control unit adds the input shortcut command to a predetermined position of the scripts.

The determination unit may include a converting unit to convert the received voice command into a text format, and an inference unit to infer the converted command.

If the voice command is repeated the predetermined number of times during a predetermined time, the control unit may register the shortcut command corresponding to the voice command after the voice command is repeated the predetermined number of times.

If a plurality of different voice commands are input the predetermined number of times within a predetermined time interval, the control unit may register a single shortcut command to perform operations corresponding to the plurality of voice commands.

The robot apparatus may further include an analyzing unit to analyze words of the voice command received from the input unit, wherein if it is determined that the voice command is repeated the predetermined number of times, the control unit combines the analyzed words, generates the shortcut command, and automatically registers the generated shortcut command to correspond to the voice command.

To achieve the above and/or other aspects and advantages, embodiments of the present invention include a method for registering a shortcut command, including receiving a voice command from a user, determining whether the voice command is repeated a predetermined number of times, and registering a shortcut command to shorten the voice command, if it is determined that the voice command is repeated the predetermined number of times.

The method may further include operating according to the voice command, wherein if the registered shortcut command is input through the receiving, the operating operates according to the voice command corresponding to the shortcut command which is received.

If it is determined that the voice command is repeated the predetermined number of times, the method may further include inquiring as to whether to register the shortcut command to shorten the voice command of the user.

The registering may receive the shortcut command to be registered in response to the inquiry.

The method may further include storing a plurality of scripts including a command, an operation performed according to the command, a subject of the operation, a condition for performing the operation, and a number of times the command is input, wherein if the shortcut command is input, the registering adds the input shortcut command to a predetermined position of the scripts.

The determining may include converting the received voice command into a text format, and inferring the converted command.

If the voice command is repeated the predetermined number of times during a predetermined time, the registering may register the shortcut command corresponding to the voice command after the voice command is repeated the predetermined number of times.

If a plurality of different voice commands are input the predetermined number of times within a predetermined time interval, the registering may register a single shortcut command to perform operations corresponding to the plurality of voice commands.

The method may further include analyzing words of the voice command received from the receiving, wherein if it is determined that the voice command is repeated the predetermined number of times, the registering combines the analyzed words, generates the shortcut command, and automatically registers the generated shortcut command to correspond to the voice command.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF EMBODIMENTS

Reference will now be made in detail to the embodiments, examples of which are illustrated in the accompanying drawings, wherein like reference numerals refer to the like elements throughout. The embodiments are described below to explain the present invention by referring to the figures.

Figure 1:
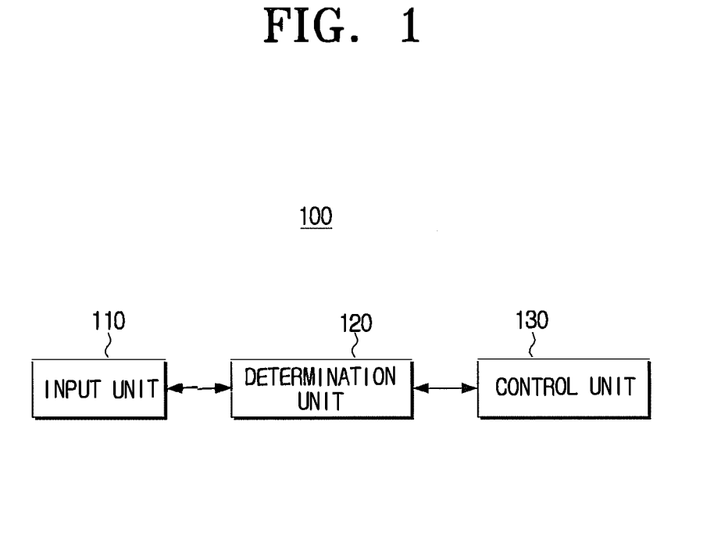
FIG. 1 is a block diagram of a robot apparatus according to an embodiment of the present invention.

FIG. 1 is a block diagram of a robot apparatus according to an embodiment of the present invention. Referring to FIG. 1, a robot apparatus 100 according to an embodiment of the present invention may include an input unit 110, a determination unit 120, and a control unit 130.

The input unit 110 receives a voice command from a user. The input unit 110 may be implemented using various input apparatuses such as a microphone. The voice command in an embodiment of the present invention is used to command a robot to perform a predetermined task, and can be, for example, a sentence such as "get me a glass of water from the dining room."

The determination unit 120 determines whether a voice command is repeated up to a predetermined number of times.

If it is determined that a voice command is repeated the predetermined number of times, the control unit 130 registers a shortcut command to shorten a voice command of a user. The shortcut command is a command in which a user can shorten a voice command such as "get me a glass of water from the dining room," and can be, for example "get me water" or "water."

The robot apparatus 100 according to an embodiment of the present invention may be a humanoid robot which operates in response to a user voice command, but should not be considered limited to a biped walking robot or a quadruped walking robot.

Figure 2:
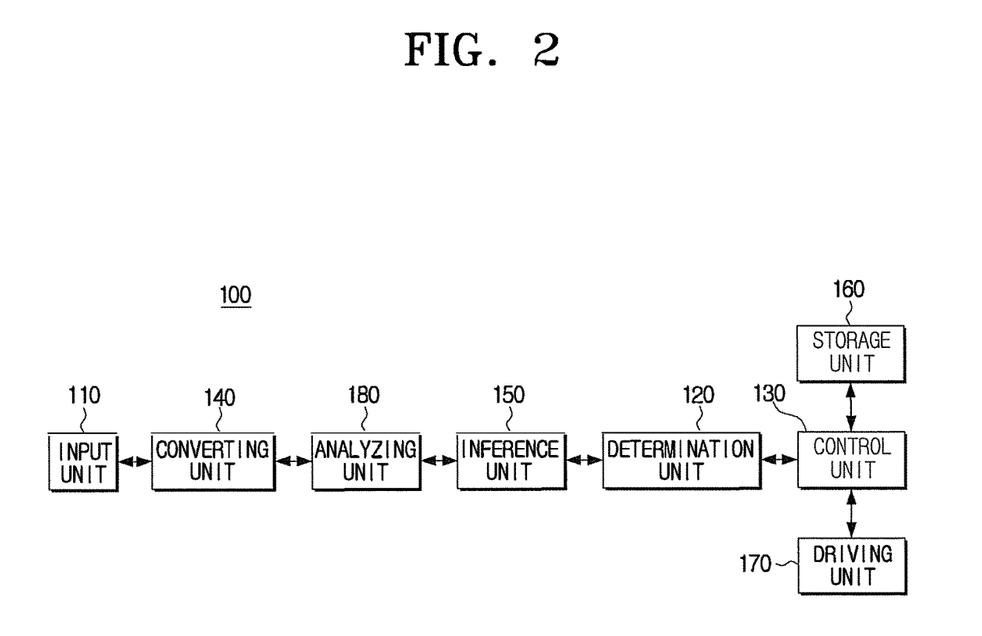
FIG. 2 is a detailed block diagram of the robot apparatus of FIG. 1.

FIG. 2 is a detailed block diagram of the robot apparatus of FIG. 1. Referring to FIG. 2, the robot apparatus 100 according to an exemplary embodiment of the present invention may further include a converting unit 140, an inference unit 150, a storage unit 160, and a driving unit 170 in addition to the input unit 110, the determination unit 120, and the control unit 130.

The converting unit 140 may convert a voice command received through the input unit 110 into a text format. The converting unit 140 may convert a voice command spoken by a user into a text format such as a programming code which the robot apparatus 100 can recognize.

The inference unit 150 may infer the meaning of a converted voice command. The inference unit 150 includes an inference engine, and infers from the task to be executed the converted voice command. The inference unit 150 may infer the converted voice command in the case that the voice command is converted into a text format or a programming language.

The inference unit 150 may select at least one of a plurality of scripts stored in the storage unit 160 according to the inferred command. The detailed structure and function of the script will be explained with reference to FIGS. 3A-3C, 4A-4C, and 5A-5B.

The storage unit 160 may store a command, an operation performed according to the command, a subject of the operation, and a plurality of scripts having conditions for performing the operation and the number of times the command is input. The storage unit 160 may store scripts in which a shortcut command is registered in a predetermined area of the script. The storage unit 160 may include in other areas, an action script pool having scripts which cause tasks to be performed and an action script pool having scripts to which shortcut commands are registered.

The scripts to which shortcut commands are registered may not be prestored, but the scripts which cause tasks to be performed may preferably be prestored in the robot apparatus 100. The storage unit 160 may prestore information required to perform tasks, for example the specific location or the position of glass. For example, if the robot apparatus 100 receives a voice command "get me a cup from the dining room" from a user, the robot apparatus 100 determines the prestored location of dining room and the prestored position of a cup, and delivers the cup to the user.

The driving unit 170 operates according to a voice command received from a user. Specifically, if the driving unit 170 receives a registered shortcut command through the input unit 110, the driving unit 170 may be controlled so as to operate according to the voice command corresponding to the received shortcut command. For example, if a shortcut command "get me a cup" is registered for a voice command "get me a cup from the dining room," and if the driving unit 170 receives a shortcut command "get me a cup," the driving unit 170 drives a motor operating its legs (not shown), which enable the robot apparatus 100 to move, and arms (not shown), which enable the robot apparatus 100 to grasp a cup, so that the robot apparatus 100 delivers a cup from the dining room.

The robot apparatus 100 according to an embodiment of the present invention may further include an analyzing unit 180 in addition to the aforementioned components 110 to 170.

The analyzing unit 180 may analyze words of a voice command received from the input unit 110. If a voice command is received, for example a user utters a sentence "get me a cup from the dining room", the analyzing unit 180 combines words such as a verb "get" or an object "cup" necessarily required in order that the robot apparatus 100 performs the task corresponding to the voice command, and generates a shortcut command. The robot apparatus 100 automatically generates a shortcut command without inquiring whether a user desires to register a shortcut command, and without receiving a sentence to be used as a shortcut command from a user.

A shortcut command generated to correspond to the received voice command may be automatically registered in a script. The analyzing unit 180 may be implemented using a context analyzer, and may be disposed between the converting unit 140 and the inference unit 150. The other components 110 to 170 are the same as the aforementioned components, and thus detailed description will be omitted.

FIGS. 3A-3C, 4A-4C, and 5A-5B illustrate scripts to register a shortcut command according to an embodiment of the present invention.

Figure 3A:
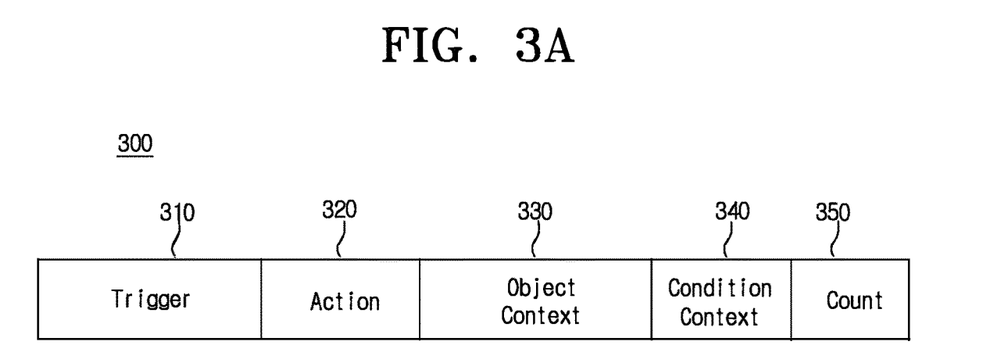
FIGS. 3A-3C, 4A-4C, and 5A-5B illustrate scripts to register a shortcut command according to an embodiment of the present invention.
Figure 3B:
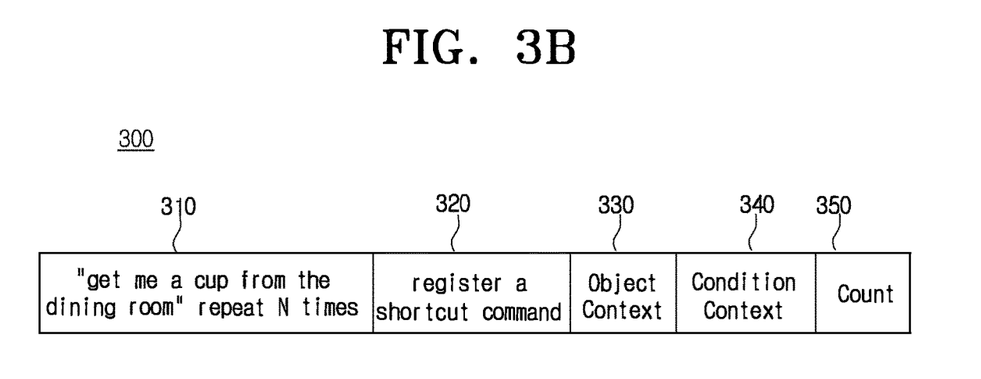
Figure 3C:
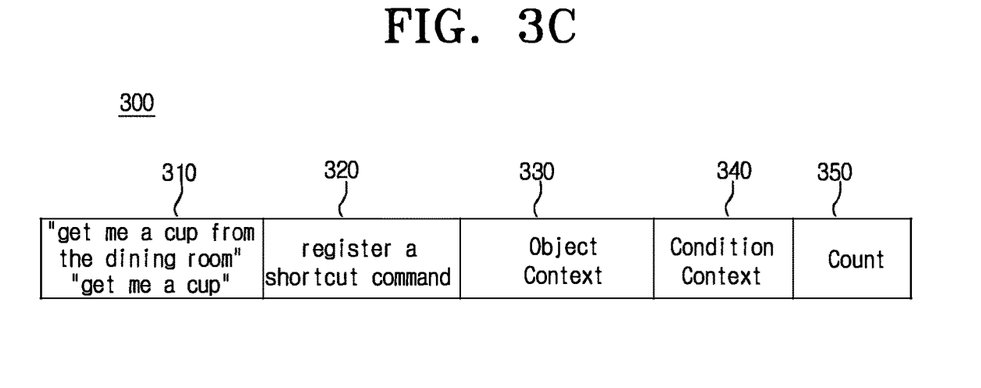

Referring to FIGS. 3A to 3C, scripts 300 stored in the storage unit 160 of the robot apparatus 100 may include a trigger area, which will be referred to hereafter as a first area 310, an action area, which will be referred to hereafter as a second area 320, an object context area, which will be referred to hereafter as a third area 330, a condition context area, which will be referred to hereafter as a fourth area 340, and a count area, which will be referred to hereafter as a fifth area 350.

For example, the first area 310 may include a command "get me a cup from the dining room," the second area 320 may include an operation, such as an action or registration of a shortcut command, corresponding to the command, the third area 330 may include an object corresponding to the operation, the fourth area 340 may include the conditions to perform the operation, and the fifth area 350 may include the number of input commands.

The operational principle according to an embodiment of the present invention will be explained in detail for the situation in which the predetermined number of input commands is two. If the input unit 110 receives a voice command "get me a cup from the dining room" for the first time, the input unit 110 does not satisfy the condition, that is the predetermined number of input commands. In this case, the inference unit 150 may select a specific script to perform the operation stored in the storage unit 160. The driving unit 170 may drive a predetermined part such as the legs (not shown) and arms (not shown) of the robot apparatus 100 so that the above operation is performed. The fifth area 350 of the script 300 performing the above operation stores the number of input voice commands.

After doing so, if a voice command "get me a cup from the dining room" is input for the second time, the determination unit 120 may refer to the number of voice commands stored in the fifth area 350 of the script 300. The number of input voice commands satisfies the predetermined number of input commands, namely two. The script 300 processes the operation for registering a shortcut command. The operation for registering a shortcut command represents the operation of adding a shortcut command, for example "get me a cup," to the first area 310 of the script 300 in order to perform the task, instead of the command "get me a cup from the dining room," as shown in FIG. 3C.

Specifically, if the determination unit 120 determines that the number of input voice commands satisfies the predetermined number of input commands, the robot apparatus 100 may inquire whether to register a shortcut command to shorten a voice command of a user. The robot apparatus 100 may inquire "Would you like to register a shortcut command?," and the driving unit 170 may output the inquiry through a speaker.

If a user inputs "Yes," the robot apparatus 100 may inquire "What words do you want to use as a shortcut command," receive words "get me a cup" from the user, and add the words "get me a cup" to the first area 310 of the script 300 as a shortcut command.

If the robot apparatus 100 further includes the analyzing unit 180 in addition to the above components 110 to 170, the process of asking a user, and registering a shortcut command through a response of a user, may be simplified.

Figure 4A:
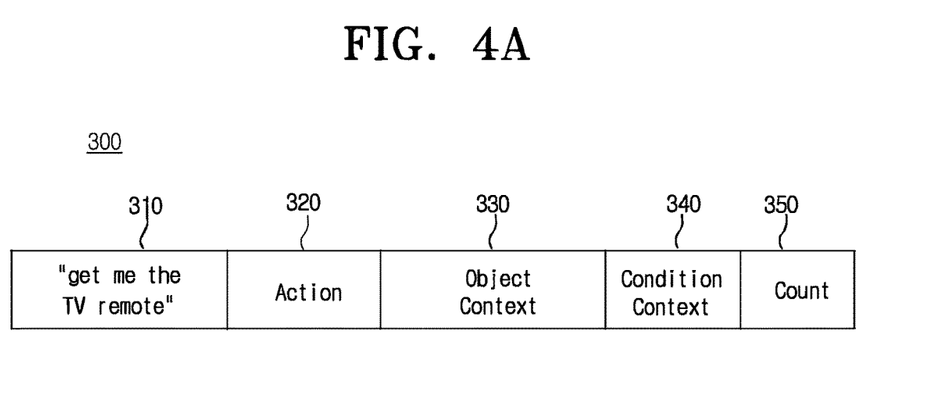
Figure 4B:
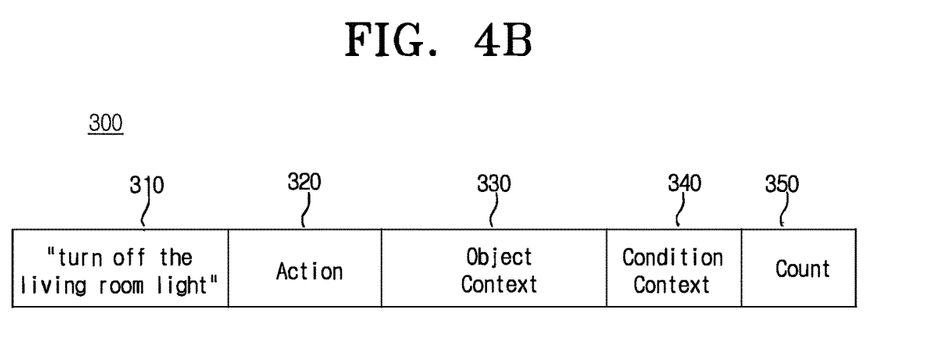
Figure 4C:
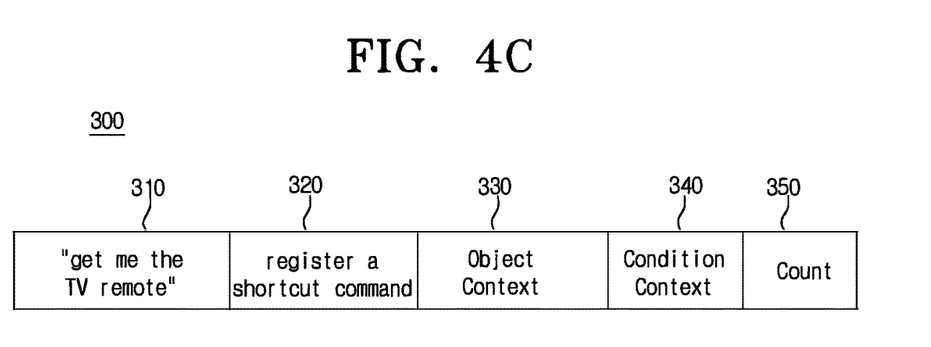

A method for determining whether a voice command is repeated up to a predetermined number of times will be described in detail with reference to FIGS. 4A-4C and 5A-5B. Referring to FIG. 4A, a voice command "get me the TV remote" is input for the first time. If the predetermined number of times is determined to be two, the robot apparatus 100 then performs tasks, that is, the robot apparatus 100 delivers the TV remote to a user, since the number of input voice commands does not satisfy the predetermined number of times. Referring to FIG. 4B, if a user inputs a voice command "turn off the living room light," the robot apparatus 100 performs the task of turning off the light of the living room according to the script 300 since the number of input voice commands still does not satisfy the predetermined number of times. If a user inputs a voice command "get me the TV remote" for the second time as shown in FIG. 4C, the control unit 130 may register a shortcut command since the number of input voice commands satisfies the predetermined number of times.

If a voice command is successively repeated as many as the predetermined number of times as shown in FIGS. 3A to 3C, a shortcut command may be registered. If a voice command is discontinuously repeated as shown in FIGS. 4A to 4C, a shortcut command may also be registered. Specifically, if a voice command of FIG. 4B different from voice commands of FIGS. 4A and 4C is inserted between the same repeated voice commands of FIGS. 4A and 4C, and if the number of repeated voice commands satisfies the predetermined number of input commands, a shortcut command may be registered.

Figure 5A:
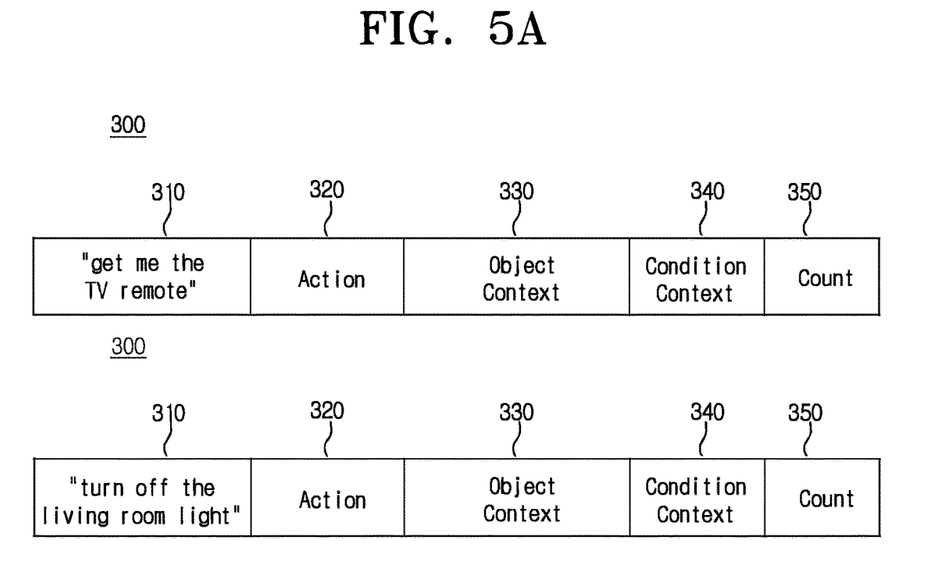
Figure 5B:
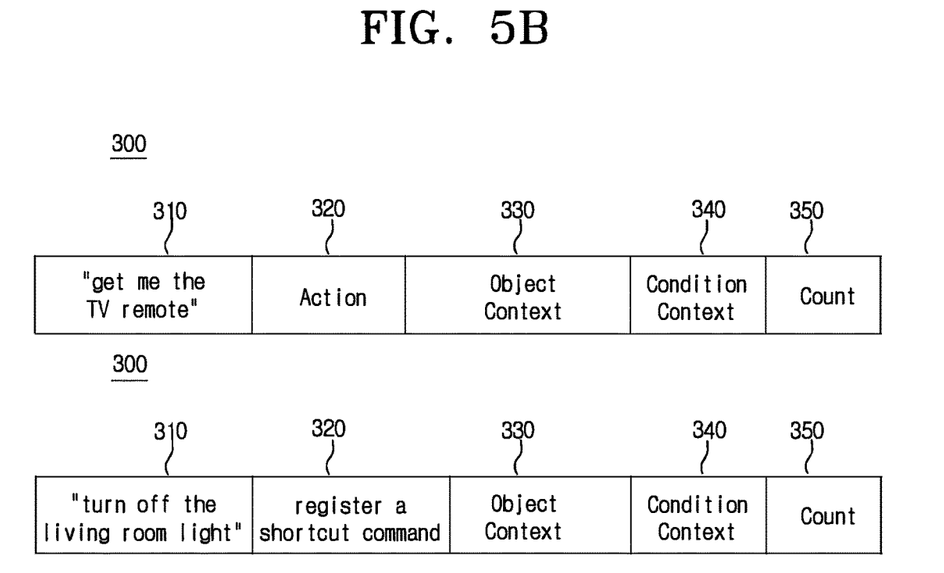

Referring to FIGS. 5A and 5B, if a plurality of different voice commands are input, and if the number of input voice commands satisfies the predetermined number of times, the robot apparatus 100 may register a shortcut command to collectively perform respective tasks corresponding to the plurality of voice commands.

For example, if the predetermined number of times is defined two, and if voice commands "get me the TV remote" and "turn off the living room light" are input, the driving unit 170 drives the robot apparatus 100 to perform the tasks corresponding to the commands.

If a voice command "get me the TV remote" is input again, the robot apparatus 100 may ask a user whether to register a shortcut command for the voice command "get me the TV remote" since the command "get me the TV remote" is repeated the predetermined number of times.

If the voice command "turn off the living room light" is input again, the robot apparatus 100 may also ask a user whether to register a shortcut command for the voice command "turn off the living room light."

If voice commands "get me the TV remote" and "turn off the living room light" are sequentially input within a predetermined time interval after the voice commands "get me the TV remote" and "turn off the living room light" are input, the robot apparatus 100 may be controlled to register a shortcut command to collectively perform tasks corresponding to the plurality of voice commands irrespective of whether shortcut commands are registered for the respective voice commands.

A shortcut command to collectively perform the tasks corresponding to the plurality of voice commands may be registered by determining whether a plurality of voice commands are repeated the predetermined times within the predetermined time interval.

If voice commands "get me the TV remote," "turn off the living room light," and "get me the TV remote" are sequentially input, and if the voice command "turn off the living room light" is input within the predetermined time interval, the robot apparatus 100 may first perform the process of registering a shortcut command to perform tasks corresponding to the plurality of voice commands. If the voice command "turn off the living room light" is repeated the predetermined number of times, the robot apparatus 100 may ask the user whether to register a shortcut command for the command "turn off the living room light."

The process of registering a shortcut command of FIGS. 5A and 5B is different from that of FIGS. 3A-3C and 4A-4C, in that a shortcut command of FIGS. 5A and 5B is registered for collected tasks corresponding to a plurality of voice commands, and a shortcut command of FIGS. 3A-3C and 4A-4C is registered for a task corresponding to a single voice command.

Figure 6:
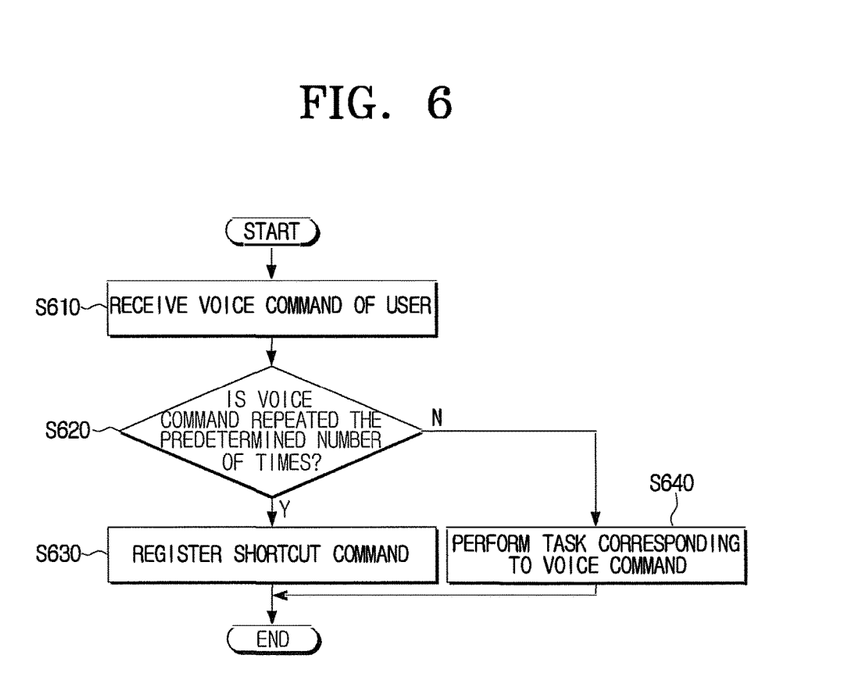
FIG. 6 is a flowchart provided to explain the process for registering a shortcut command according to an embodiment of the present invention.

FIG. 6 is a flowchart provided to explain the process for registering a shortcut command according to an embodiment of the present invention. Referring to FIG. 6, a method for registering a shortcut command according to an embodiment of the present invention is provided. The input unit 110 receives a voice command of a user in operation S610, and the determination unit 120 determines whether the voice command is repeated the predetermined number of times in operation S620. If it is determined that the voice command is repeated the predetermined number of times in as shown by the path (Y), the control unit 130 registers a shortcut command in operation S630. If it is determined that the voice command is not repeated the predetermined number of times as shown by the path (N), the control unit 130 causes the robot apparatus 100 to perform the task corresponding to the voice command in operation S640.

Figure 7:
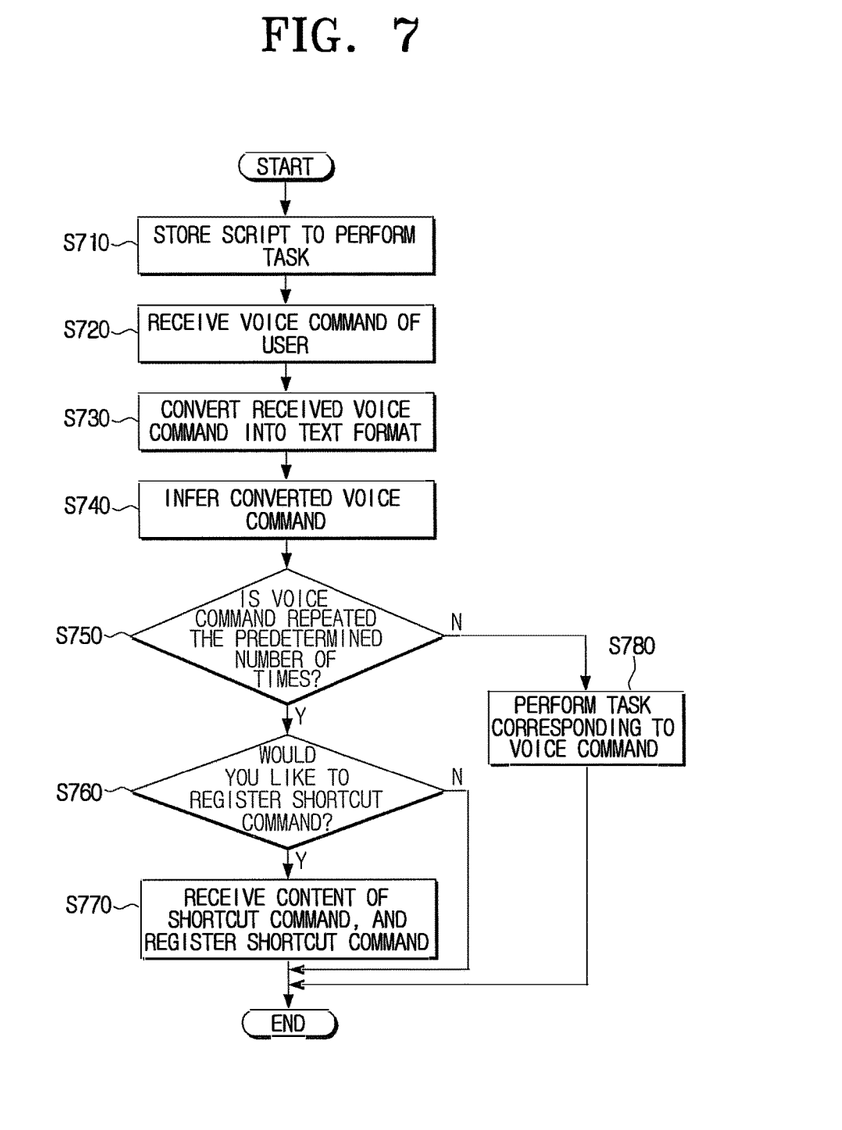
FIG. 7 is a detailed flowchart provided to explain the process for registering a shortcut command of FIG. 6.

FIG. 7 is a detailed flowchart provided to explain the process for registering a shortcut command of FIG. 6. Referring to FIG. 7, a method for registering a shortcut command according to an embodiment of the present invention includes the processes of storing a script to perform a task in operation S710, and receiving a voice command of a user in operation S720. The received voice command is converted into a text format in operation S730. The method includes the processes of inferring the converted voice command, and selecting a script corresponding to the task from among the stored scripts in operation S740.

It is determined whether the voice command is repeated the predetermined number of times in operation S750, and if the voice command is repeated the predetermined number of times, following the path (Y), whether to register a shortcut command is inquired in operation S760. A shortcut command is registered by receiving words to be a shortcut command in operation S770.

If the voice command is not repeated the predetermined number of times as shown in path (N), the task corresponding to the voice command is performed in operation S780.

Figure 8:
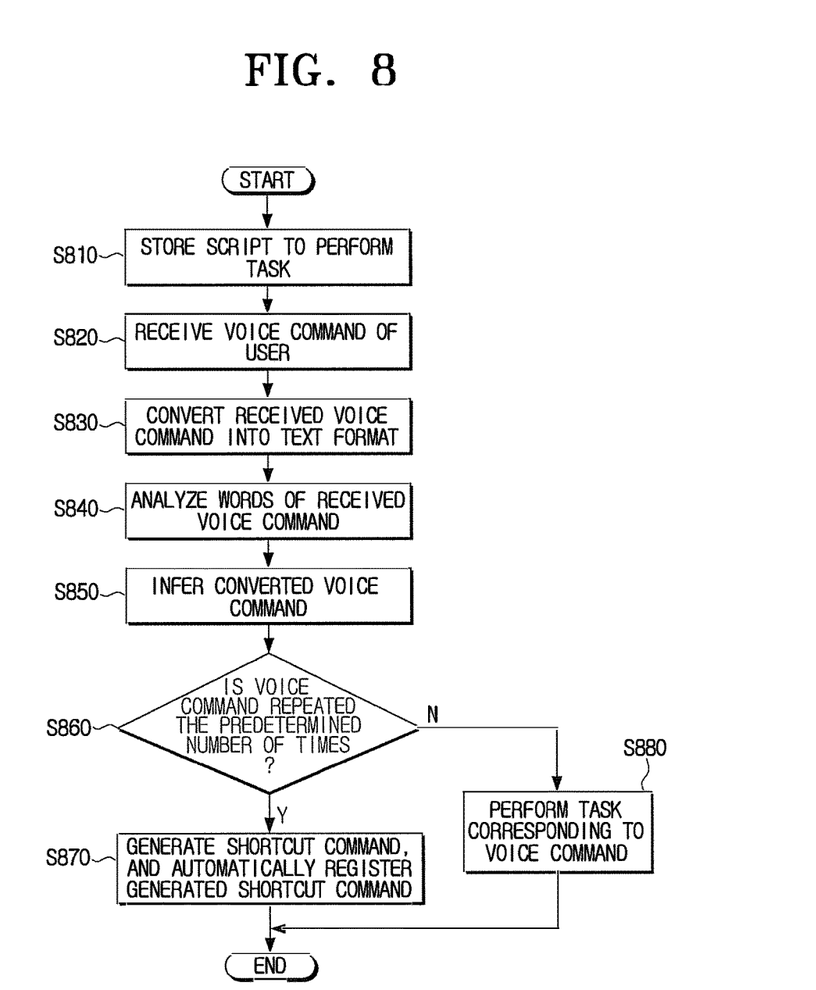
FIG. 8 is a flowchart provided to explain the process for registering a shortcut command.

FIG. 8 is a flowchart provided to explain the process for registering a shortcut command. Referring to FIG. 8, a script to perform a task is stored in operation S810, a voice command of a user is received in operation S820, and the received voice command is converted into a text format in operation S830. The words of the received voice command are analyzed in operation S840, and the converted voice command is inferred in operation S850.

It is determined whether the voice command is repeated the predetermined number of times in operation S860. If it is determined that the voice command is repeated the predetermined number of times, as shown in path (Y), a shortcut command is generated, and the generated shortcut command is automatically registered in operation S870.

If it is determined that the voice command is not repeated the predetermined number of times, as shown in path (N), a task corresponding to the voice command is performed in operation S880.

As described above, according to embodiments of the present invention, a shortcut command to shorten a voice command of a user is generated, and thus a user can conveniently give repeated commands using shorter sentences. A point of a user voice command is transferred to a robot by using a concise command, so the robot can correctly perform tasks corresponding to the voice command.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An electronic apparatus comprising:
   a driving unit;
   an input unit;
   a storage unit storing information on a plurality of voice commands received through the input unit, wherein each of the plurality of voice commands includes a complete command phrase required to perform an operation of the electronic apparatus; and
   a control unit configured to:
   perform an operation corresponding to a voice command based on the voice command of the plurality of voice commands being received,
   identify whether different voice commands among the plurality of voice commands are received sequentially a predetermined number of times based on the information,
   receive, through the input unit, a shortcut command to shorten the different voice commands based on the different voice commands being received sequentially the predetermined number of times within a predetermined time interval,
   register the shortcut command to the storage unit, and
   based on a voice command corresponding to the registered shortcut command being received through the input unit, control the driving unit to perform different operations which respectively correspond to the different voice commands.

2. The apparatus of claim 1, wherein if the different voice commands are received the predetermined number of times, the control unit inquires whether to register the shortcut command to shorten the different voice commands.

3. The apparatus of claim 2, wherein the control unit receives the shortcut command to be registered in response to the inquiry.

4. The apparatus of claim 3, wherein the storage unit further stores a plurality of scripts including a command, an operation performed according to the command, a subject of the operation, and a condition for performing the operation,
wherein if the shortcut command is input, the control unit adds the input shortcut command to a predetermined position of the scripts.

5. The apparatus of claim 1, wherein the control unit is further configured to:
convert the received voice command into a text format; and
infer the converted command.

6. The apparatus of claim 1, wherein if the different voice commands are received sequentially the predetermined number of times during a predetermined time, the control unit registers the shortcut command corresponding to the different voice commands after the different voice commands are received the predetermined number of times.

7. The apparatus of claim 1, wherein the control unit is further configured to:
analyze words of the different voice commands received sequentially through the input unit, and
if the different voice commands are received sequentially the predetermined number of times, combine the analyzed words, generate the shortcut command, and automatically register the generated shortcut command.

8. A method for registering a shortcut command of an electronic apparatus, the method comprising:
receiving a plurality of voice commands;
storing information on the plurality of voice commands, wherein each of the plurality of voice commands includes a complete command phrase required to perform an operation of the electronic apparatus;
performing an operation corresponding to a voice command based on the voice command of the plurality of voice commands being received;
identifying whether different voice commands among the plurality of voice commands are received sequentially a predetermined number of based on the information;
receiving a shortcut command to shorten the different voice commands, based on the different voice commands being received sequentially the predetermined number of times within a predetermined time interval;
registering the shortcut command; and
based on a voice command corresponding to the registered shortcut command being received, performing different operations which respectively correspond to the plurality of different voice commands.

9. The method of claim 8, wherein if the different voice commands are received sequentially the predetermined number of times, inquiring whether to register the shortcut command to shorten the different voice commands.

10. The method of claim 9, wherein the registering receives the shortcut command to be registered in response to the inquiry.

11. The method of claim 10, further comprising:
storing a plurality of scripts including a command, an operation performed according to the command, a subject of the operation, and a condition for performing the operation,
wherein if the shortcut command is input, the registering adds the input shortcut command to a predetermined position of the scripts.

12. The method of claim 8, further comprising:
converting the received voice command into a text format; and
inferring the converted command.

13. The method of claim 8, wherein if the different voice commands are received sequentially the predetermined number of times during a predetermined time, the registering registers the shortcut command corresponding to the different voice commands after the different voice commands are received the predetermined number of times.

14. The method of claim 8, further comprising:
analyzing words of the different voice commands received sequentially,
wherein if the different voice commands are received sequentially the predetermined number of times, the registering combines the analyzed words, generates the shortcut command, and automatically registers the generated shortcut command.

* * * * *

UNITED STATES PATENT AND TRADEMARK OFFICE
CERTIFICATE OF CORRECTION

PATENT NO. : 10,438,589 B2
APPLICATION NO. : 15/958349
DATED : October 8, 2019
INVENTOR(S) : Hyun-ryong Jung Page 1 of 1

It is certified that error appears in the above-identified patent and that said Letters Patent is hereby corrected as shown below:

In the Claims

Column 9, Line 44:
Claim 8, after "number of" insert -- times --.

Column 10, Line 9:
Claim 8, after "correspond to the" delete "plurality of".

Signed and Sealed this
Seventh Day of January, 2020

Andrei Iancu
*Director of the United States Patent and Trademark Office*